US008729501B2

(12) United States Patent
Ogawa

(10) Patent No.: US 8,729,501 B2
(45) Date of Patent: May 20, 2014

(54) ULTRAVIOLET IRRADIATION DEVICE FOR IMPLANTS

(75) Inventor: Yoshimasa Ogawa, Himeji (JP)

(73) Assignee: Ushio Denki Kabushiki Kaisha, Chiyoda-Ku, Tokyo (JP)

(*) Notice: Subject to any disclaimer, the term of this patent is extended or adjusted under 35 U.S.C. 154(b) by 0 days.

(21) Appl. No.: 13/991,568

(22) PCT Filed: Oct. 18, 2011

(86) PCT No.: PCT/JP2011/073921
§ 371 (c)(1),
(2), (4) Date: Jun. 4, 2013

(87) PCT Pub. No.: WO2012/105094
PCT Pub. Date: Aug. 9, 2012

(65) Prior Publication Data
US 2013/0264495 A1 Oct. 10, 2013

(30) Foreign Application Priority Data

Jan. 31, 2011 (JP) ................................ 2011-017434

(51) Int. Cl.
A61L 2/10 (2006.01)
(52) U.S. Cl.
USPC .................................. 250/455.11; 250/504 R
(58) Field of Classification Search
None
See application file for complete search history.

(56) References Cited

U.S. PATENT DOCUMENTS 5,029,252 A * 7/1991 Ameseder ................ 250/455.11
5,547,635 A * 8/1996 Duthie, Jr. ...................... 422/24
5,554,024 A * 9/1996 Ueda ............................... 433/37
5,688,475 A * 11/1997 Duthie, Jr. ................. 422/186.3
6,402,517 B1 * 6/2002 Hozumi et al. ............. 433/201.1
6,605,260 B1 * 8/2003 Busted ....................... 422/186.3
7,280,870 B2 * 10/2007 Nurmikko et al. ............. 607/37
7,435,084 B2 * 10/2008 Liu et al. ......................... 433/34
7,798,159 B2 * 9/2010 Palfy et al. ..................... 134/184
8,002,897 B2 * 8/2011 Palfy et al. ......................... 134/1
2004/0099812 A1 * 5/2004 Humphreys et al. ...... 250/455.11
2004/0118427 A1 * 6/2004 Palfy et al. ......................... 134/1
2006/0127859 A1 * 6/2006 Wen ............................... 433/213
2009/0322190 A1 * 12/2009 Kitagawa et al. ............. 312/206
2010/0269852 A1 * 10/2010 Palfy et al. ......................... 134/1
2010/0269861 A1 * 10/2010 Palfy et al. ....................... 134/18

FOREIGN PATENT DOCUMENTS

| DE | 19544392 A1 * | 7/1996 | ............... A61L 2/02 |
| EP | 0 079 827 A1 * | 5/1983 | ............... A61L 2/20 |
| EP | 0 313 409 A2 | 4/1989 | |
| EP | 2 140 885 A1 | 1/2010 | |

(Continued)

Primary Examiner — Andrew Smyth
(74) Attorney, Agent, or Firm — Fitzpatrick, Cella, Harper & Scinto

(57) ABSTRACT

Disclosed herein is an ultraviolet irradiation device for removing organic contaminants from implants using ultraviolet rays. In the present invention, the implants can be easily and smoothly put into or pulled out of a processing chamber, and the implants can be reliably prevented from being recontaminated after the ultraviolet irradiation process has finished. For this, the ultraviolet irradiation device includes a housing provided with an openable door, an ultraviolet lamp installed in the housing, a carriage provided in the housing so as to be extractable, and an implant mount unit placed on the carriage in such a way that the implant mount unit can be disposed facing the ultraviolet lamp in the housing. The implant mount unit includes a mounting board removably placed on the carriage, and an implant support removably placed on the mounting board.

5 Claims, 7 Drawing Sheets

(56) References Cited

FOREIGN PATENT DOCUMENTS

| | | | | |
|---|---|---|---|---|
| EP | 2140885 A1 * | 1/2010 | ............ | A46B 17/06 |
| JP | 58-221949 A | 12/1983 | | |
| JP | 01-207070 A | 8/1989 | | |
| JP | 01207070 A * | 8/1989 | ................ | A61L 2/10 |
| JP | 04-264723 A | 9/1992 | | |
| JP | 04264723 A * | 9/1992 | ............ | H01L 21/304 |
| JP | 8-121784 A | 5/1996 | | |
| JP | 2000-066003 A | 3/2000 | | |
| JP | 2000066003 A * | 3/2000 | ............... | G02B 1/10 |
| JP | 3072373 B1 | 6/2000 | | |
| JP | 3144409 B2 * | 3/2001 | ............ | A61C 13/15 |
| JP | 2005-342314 A | 12/2005 | | |
| JP | 2005342314 A * | 12/2005 | ................ | A61L 2/20 |
| JP | 3144409 U * | 8/2008 | ............ | A61C 13/15 |

\* cited by examiner

ULTRAVIOLET IRRADIATION DEVICE FOR IMPLANTS

TECHNICAL FIELD

The present invention relates to ultraviolet irradiation devices for applying ultraviolet rays to implants to remove organic contaminants therefrom and, in particular, to an ultraviolet irradiation device for removing organic contaminants from dental implants using an ultraviolet lamp.

BACKGROUND ART

Generally, implants, particularly, dental implants, are embedded in jaw bones to be substituted for the function of teeth. In a dental implant operation, it is important to reliably fuse a dental implant to a jaw bone (for osseointegration). To achieve this purpose, for example, a technique of applying ultraviolet rays to dental implants and removing organic contaminants from the dental implants was proposed in Japanese Patent No. 3072373 (Patent document 1) and described in paragraph 0009 of the document.

However, the technique disclosed in this document was proposed merely theoretically, and the detailed construction of a device to embody the technique was not proposed.

With regard to a dental implant operation, after the process of applying ultraviolet rays to a dental implant and removing organic contaminants therefrom has been completed, the dental implant must be used in the dental implant operation as soon as possible to prevent the dental implant from being recontaminated by organic contaminants.

Therefore, it is necessary to be able to easily and smoothly put implants into an ultraviolet irradiation device or take them out of it, and to reliably prevent the implants from being recontaminated after the ultraviolet irradiation process has finished.

To date, a small and simple device for removing organic contaminants from implants while preventing recontamination of the implants has not been put to practical use.

PRIOR ART DOCUMENT

Patent Document

Patent document 1: Japanese Patent No. 3072373

DISCLOSURE

Technical Problem

Accordingly, the present invention has been made keeping in mind the above problems occurring in the prior art, and an object of the present invention is to provide an ultraviolet irradiation device for removing organic contaminants from implants such as artificial dental roots using an ultraviolet lamp that emits ultraviolet rays, wherein the implants can be easily and smoothly put into or pulled out of a processing chamber, and the implants can be reliably prevented from being recontaminated after the ultraviolet irradiation process has finished.

Technical Solution

In order to accomplish the above object, the present invention provides an ultraviolet irradiation device for removing organic contaminant from an implant using ultraviolet rays, the ultraviolet irradiation device including: a housing provided with an openable door; an ultraviolet lamp installed in the housing; a carriage provided in the housing so as to be extractable; and an implant mount unit placed on the carriage in such a way that the implant mount unit can be disposed facing the ultraviolet lamp in the housing, the implant mount unit comprising: a mounting board removably placed on the carriage; and an implant support removably placed on the mounting board.

The carriage may be extracted from or retracted into the housing in conjunction with opening or closing of the door.

Preferably, a handle may be installed on the mounting board.

In addition, means for positioning the mounting board may be provided on the carriage.

Further, means for positioning the implant support may be provided on the mounting board.

Furthermore, an insert hole may be formed in the implant support so that the implant is inserted into the insert hole and supported by the implant support.

Advantageous Effects

In an ultraviolet irradiation device for implants according to the present invention, an implant mount unit which supports implants includes a mounting board and an implant support and is mounted on a carriage which can be extracted from a housing or retracted thereinto. Therefore, the implant mount unit can be divided into a clean area and an unclean area. When a process of applying ultraviolet rays to the implants is carried out, a worker has only to handle the mounting board that forms the unclean area, without touching the implant support that forms the clean area, whereby the implants that are in the clean area can be kept clean and are prevented from being recontaminated after the ultraviolet irradiation process has finished.

Furthermore, in a sterilization process before the ultraviolet irradiation process, only the implant support which forms the clean area needs to be sterilized. Consequently, a comparatively large number of units to be sterilized can be contained in a sterilization device. As a result, the sterilization process can be more efficiently carried out.

In addition, since the implant mount unit is mounted to the carriage that is operated in conjunction with a door of the housing, when the door is closed, the implants can be reliably disposed at correct positions facing an ultraviolet lamp and then ultraviolet radiation process can be effectively carried out.

BEST MODE

Figure 1:
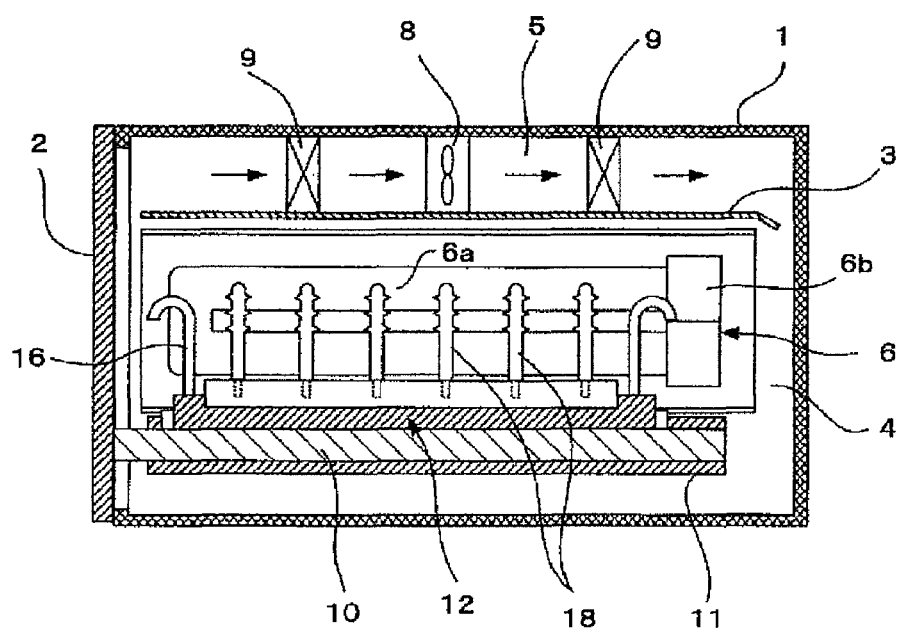
FIG. 1 is a side sectional view of an ultraviolet irradiation device for dental implants, according to the present invention.

As shown in FIG. 1, an ultraviolet irradiation device for dental implants according to the present invention includes a sealed housing 1, and a door 2 which airtightly closes the housing 1 or opens it. A space defined by the housing 1 is partitioned into a main processing chamber 4 and an ozone processing chamber 5 by a partition wall 3. An ultraviolet lamp 6 is installed in the main processing chamber 4.

The ultraviolet lamp 6 is a lower pressure mercury lamp which emits ultraviolet rays having wavelengths, for example, ranging from 185 nm to 254 nm The ultraviolet lamp 6 includes a U-shaped light emitting tube 6a which has two linear parts that extend in the longitudinal direction of the housing 1 and are connected to a curved part. The light emitting tube 6a is configured such that the two linear parts are disposed at upper and lower positions and the longitudinal direction of the linear parts are oriented in an approximate horizontal direction. A base 6b is mounted to an end of the light emitting tube 6a.

Figure 2:
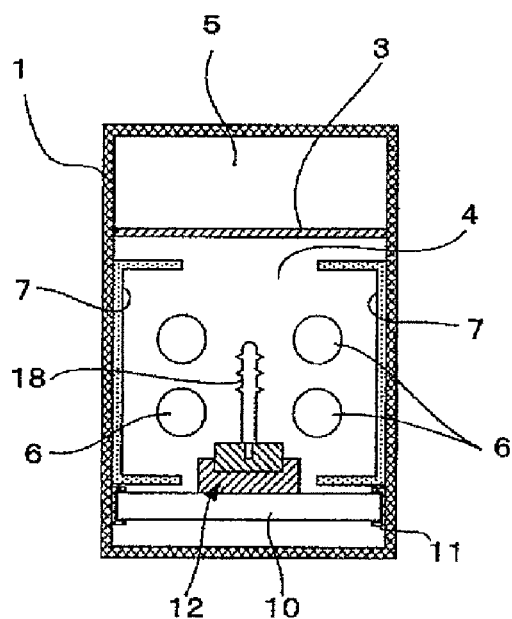
FIG. 2 is a cross-sectional view of FIG. 1.

As shown in FIG. 2, the ultraviolet lamp 6 comprises a pair of ultraviolet lamps 6 which are arranged to face each other. Reflective mirrors 7, each of which has a gutter-shaped cross-section, are provided on opposite sides of the ultraviolet lamps 6 to have a shape whereby they surround the ultraviolet lamps 6.

A fan 8, which circulates gas in the housing 1, and an ozone removal means 9 are installed in the ozone processing chamber 5. The ozone removal means 9 is, for example, an ozone removal filter which is provided in such a way that an ozone removal catalyst formed, for example, of manganese dioxide is contained in a frame provided with a honeycomb structure made of inorganic fiber paper.

Gas containing ozone that has been in the main processing chamber 4 flows through the ozone processing chamber 5 by means of the fan 8 and then enters the main processing chamber 4 again after ozone has been removed from the gas by the ozone removal means 9. In this way, the gas circulates.

Figure 3:
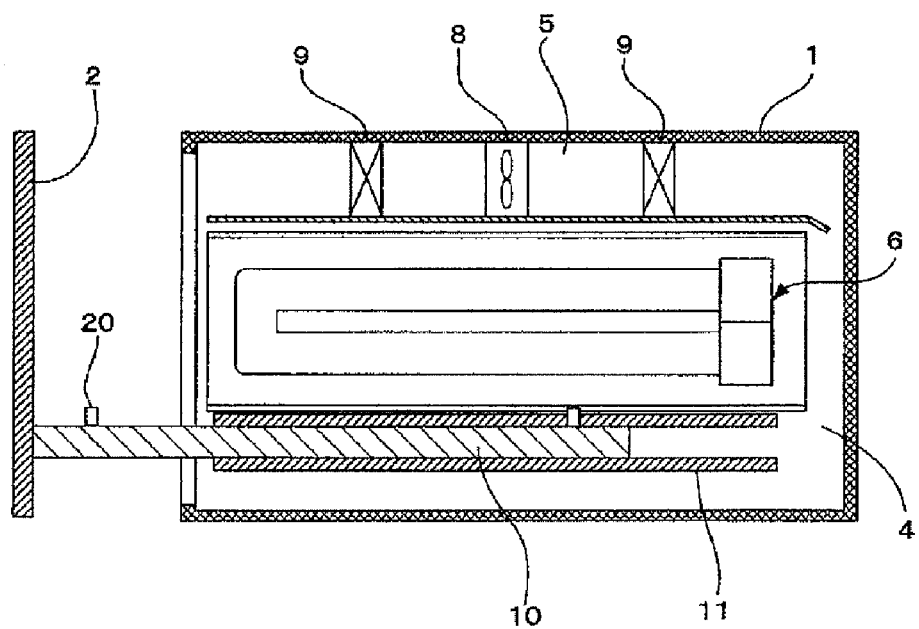
FIG. 3 is a sectional view of the ultraviolet irradiation device of FIG. 1 when a door opens.

Referring to FIG. 3 illustrating the door 2 that has been opened, in this embodiment, the door 2 has a draw-out type structure. The door 2 is integrally provided with a carriage 10. The carriage 10 is guided by a guide 11 installed in the housing 1 and is extracted from or retracted into the housing 1 in conjunction with the opening or closing operation of the door 2.

Figure 4:
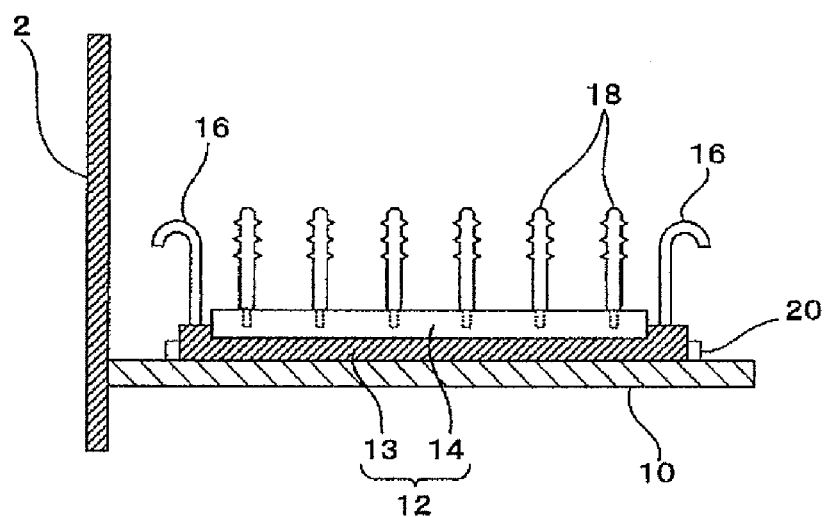
FIG. 4 is a sectional view illustrating the door and an implant mount unit of FIG. 1.

FIG. 4 illustrates an implant mount unit 12 which is disposed on the carriage 10 that is interlocked with the door 2. The implant mount unit 12 is placed on the carriage 10.

Figure 5:
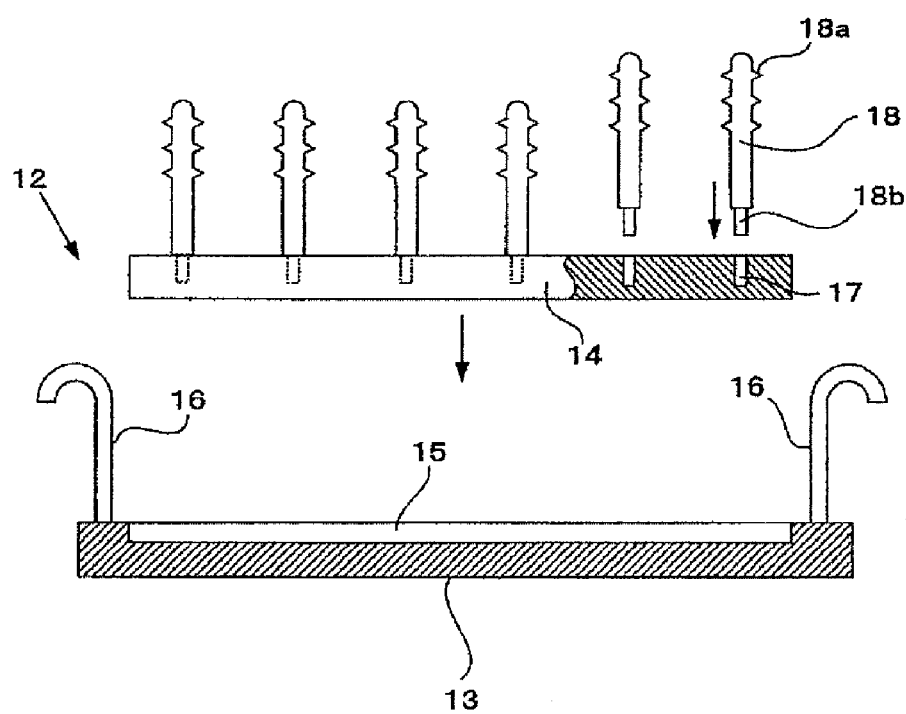
FIG. 5 is a sectional view illustrating the implant mount unit.

FIG. 5 shows in detail the implant mount unit 12. The implant mount unit 12 includes a mounting board 13 and an implant support 14. A recess 15 is formed in the mounting board 13 and functions as a means for positioning the implant support 14. Handles 16 are provided on respective opposite ends of the mounting board 13.

A plurality of insert holes 17 are formed in the implant support 14. Implants 18 are inserted into the insert holes 17 so that they can be supported by the implant support 14. Here, an end 18b of each implant 18 is inserted into the corresponding insert hole 17 such that a threaded part 18a of the implant 18 that is disposed opposite to the end 18b and is provided to be embedded in the human body is oriented upwards. After the mounting of the implants 18 has completed, the implant support 14 is inserted into the recess 15 of the mounting board 13.

As shown in FIG. 4, the implant mount unit 12 on which the implants 18 are mounted is placed onto the carriage 10 while the position thereof is determined by a positioning means 20 provided on the carriage 10.

Subsequently, as shown in FIG. 1, the door 2 is closed. Then, the implant mount unit 12 that is placed on the carriage 10 is disposed between the two ultraviolet lamps 6 such that the implants 18 can be positioned in a longitudinal effective light-emitting range of the ultraviolet lamps 6.

In this state, the implants 18 are cleaned by ultraviolet rays emitted from the ultraviolet lamps 6.

After the cleaning process has finished, the fan 8 is operated only for a predetermined time so that gas that has been in the main processing chamber 4 of the housing 1 flows into the ozone processing chamber 5 and then circulates. While the gas circulates the main processing chamber 4 and the ozone processing chamber 5, ozone is removed from the gas by the ozone removal means 9.

Figure 6:
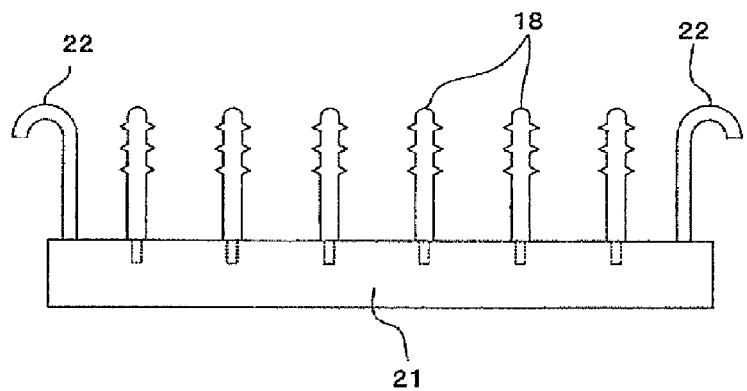
FIG. 6 illustrates a comparative example of the implant mount unit.

Because the implants must be understandably maintained clean, a worker holds the implant mount unit so as to pull the implants out of the device without directly touching the implants. To embody this, as shown in FIG. 6, the implant mount unit may be designed such that the handles 2 are provided on the implant mount unit 21, which supports the implants 18 thereon, to enable the worker to easily hold the implant mount unit 21.

Preferably, the implant mount unit 21 is made of material, for example, metal such as stainless steel, having resistance to ultraviolet rays and ozone, because it is exposed to ultraviolet rays or ozone.

When the ultraviolet irradiation is being carried out, the temperature of the implant mount unit 21 made of metal is increased to 70° C. by heat generated from the lamps. If the implant mount unit 21 is provided with the handles 22, it is not long before the worker can handle the implant mount unit 21, because the handles 22 are comparatively rapidly cooled.

In the medical field, an element such as the implant mount unit, which directly supports a member such as the implant which is used in such a way as to be embedded in the human body, is treated as a clean area, because it has been sterilized. However, as shown in FIG. 6, although the implant mount unit 21 is provided with the handles 22, if the implant mount unit 21 is configured such that the implants 18 are directly mounted to the implant mount unit 21, the worker must directly handle the implants 18. As a result, there is the high possibility of the implants 18 being recontaminated after the sterilization process has finished, despite the fact that the implant mount unit 21 forms the clean area.

Furthermore, an autoclave is used as a device for sterilizing the implant mount unit 21. Such an autoclave is a device which processes a target under high-temperature and high-pressure conductions. Therefore, in the case of the sterilization process using the autoclave, additional cooling time is required after sterilization time has passed. Overall, this entire process takes more than an hour.

Therefore, if it is necessary to successively carry out several ultraviolet irradiation processes, a plurality of implant mount units that have been sterilized are required.

Figure 7:
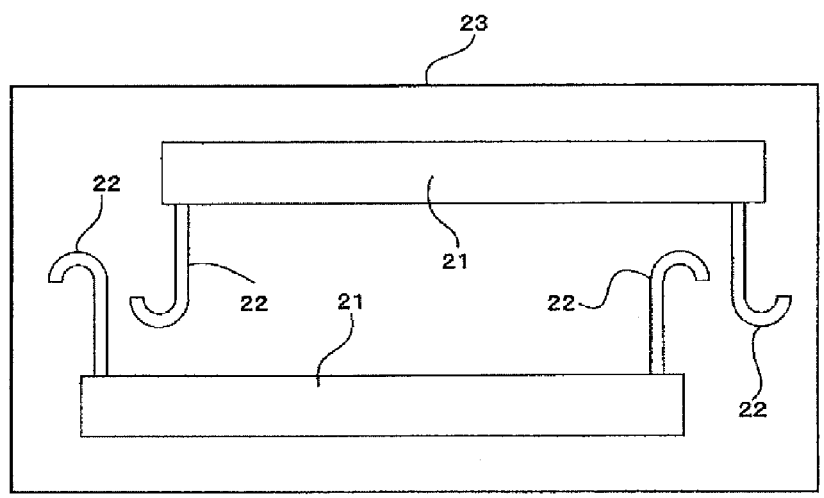
FIG. 7 is a view illustrating a sterilization process of the comparative example of FIG. 6.

Furthermore, in the case where the implant mount unit 21 is provided with the handles 22, as shown in FIG. 7, the number of implant mount units 21 that can be sterilized in the autoclave 23 during a single process is reduced, because the handles 22 take up a lot of space.

Even so, it is not economically viable to use a plurality of autoclaves. Moreover, if the autoclave has a comparatively large size, not only is the entire size of the device increased, but separate management in conformity with the occupational safety and health act is also required.

Given this, in the present invention, the implant mount unit 12 includes the mounting board 13 and the implant support 14 which are separately provided. The handles 16 are provided on the mounting board 13. The implant support 14 is designated as a clean area, while the mounting board 13 is designated as an unclean area. A target to be sterilized is only the implant support 14 that forms the clean area.

Figure 8:
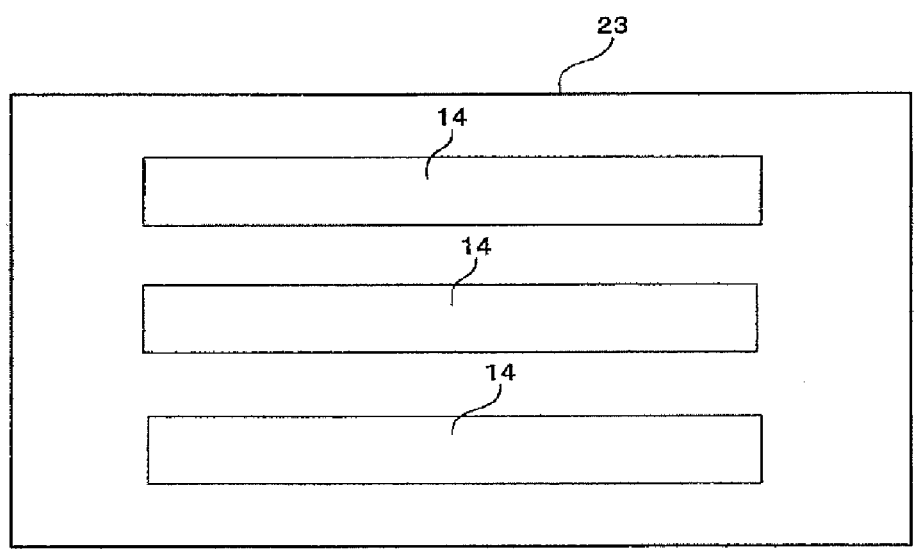
FIG. 8 is a view illustrating a sterilization process using the implant mount unit according to the present invention.

By doing this, as shown in FIG. 8, when the implant supports 14 are placed in the autoclave 23 to sterilize them, the number of implant supports 14 that can be contained therein can be increased, whereby the sterilization process can be efficiently conducted.

Meanwhile, as an example of the positioning means 20 of the carriage 10 for the implant mount unit 12, as well as a protrusion structure, a recess or the like may be used. In the same manner, as the positioning means of the mounting board 13 for the implant support 14, as well as the recess 15 illustrated in the drawings, a protrusion or the like may be used.

Furthermore, although the carriage 10 has been illustrated as being integrally provided with the door 2, they may be separately provided. In this case, the door 2 is configured to be extracted or retracted by means of a guide that is provided separately from the guide 11 associated with the carriage 10.

In addition to the draw-out type door, a swing type door using a hinge may be used as the door 2 of the housing 1. In this case, the carriage 10 onto which the implant mount unit 12 is placed may be configured such that it can be extracted from or retracted into the housing 1 separately from the opening or closing of the door 2 or, alternatively, it may be horizontally extracted from or retracted into the housing 1 in conjunction with the rotation of the door 2.

As described above, in an ultraviolet irradiation device for dental implants according to the present invention, an implant mount unit which supports implants includes a mounting board and an implant support and is mounted on a carriage which can be extracted from a housing or retracted thereinto. Therefore, the implant mount unit can be divided into a clean area and an unclean area. When a process of applying ultraviolet rays to the implants is carried out, a worker has only to handle the mounting board that forms the unclean area, whereby the implants that are in the clean area can be prevented from being recontaminated.

Furthermore, in a sterilization process before the ultraviolet irradiation process, only the implant support which forms the clean area is needed to be sterilized. Consequently, a comparatively large number of units to be sterilized can be contained in a sterilization device. As a result, the sterilization process can be more efficiently carried out.

In addition, a handle is installed on the mounting board, thus facilitating handling thereof Moreover, because the handle can be rapidly cooled even after it has been heated, it is not long before a worker can handle the implant mount unit.

Further, since the carriage is moved in conjunction with a door of the housing, the implants can be in the correct positions facing ultraviolet lamps by opening or closing of the door. Thus, the operation of processing the implants using ultraviolet rays can be facilitated.

DESCRIPTION OF THE ELEMENTS IN THE DRAWINGS

1 housing
2 door
3 partition wall
4 main processing chamber
5 ozone processing chamber
6 ultraviolet lamp
7 reflective mirror
8 fan
9 ozone removal means
10 carriage
11 guide
12 implant mount unit
13 mounting board
14 implant support
15 recess (positioning means)
16 handle
17 insert hole
18 (dental) implant
20 positioning means

The invention claimed is:

1. An ultraviolet irradiation device for removing organic contaminant from an implant using ultraviolet rays, the ultraviolet irradiation device comprising:
a housing provided with an openable door;
an ultraviolet lamp installed in the housing;
a carriage provided in the housing so as to be extractable; and
an implant mount unit that includes metal, the implant mount unit being placed on the carriage in such a way that the implant mount unit can be disposed facing the ultraviolet lamp in the housing, the implant mount unit comprising:
a mounting board removably placed on the carriage; and
an implant support removably placed on the mounting board,
wherein a handle is installed on the mounting board.

2. The ultraviolet irradiation device as set forth in claim 1, wherein the carriage is extracted from or retracted into the housing in conjunction with opening or closing of the door.

3. The ultraviolet irradiation device as set forth in claim 1, wherein means for positioning the mounting board is provided on the carriage.

4. The ultraviolet irradiation device as set forth in claim 1, wherein means for positioning the implant support is provided on the mounting board.

5. The ultraviolet irradiation device as set forth in claim 1, wherein an insert hole is formed in the implant support so that the implant is inserted into the insert hole and supported by the implant support.

* * * * *